(12) United States Patent
Woo et al.

(10) Patent No.: US 7,468,428 B2
(45) Date of Patent: Dec. 23, 2008

(54) LYOPHILIZED AZITHROMYCIN FORMULATION

(75) Inventors: Byung Ho Woo, Schaumburg, IL (US); K. Keith Kwok, Long Grove, IL (US); Kang Yong Yang, Flossmoor, IL (US)

(73) Assignee: APP Pharmaceuticals, LLC, Schaumburg, IL (US)

( * ) Notice: Subject to any disclaimer, the term of this patent is extended or adjusted under 35 U.S.C. 154(b) by 60 days.

(21) Appl. No.: 10/802,282

(22) Filed: Mar. 17, 2004

(65) Prior Publication Data

US 2005/0209172 A1    Sep. 22, 2005

(51) Int. Cl.
C07H 17/08    (2006.01)
(52) U.S. Cl. ........................................ 536/7.4
(58) Field of Classification Search ............ 514/29; 536/7.4
See application file for complete search history.

(56) References Cited

U.S. PATENT DOCUMENTS

| | | | |
|---|---|---|---|
| 2,653,899 A | 9/1953 | Bunch et al. | |
| 3,417,077 A | 12/1968 | Murphy et al. | |
| 3,478,014 A | 11/1969 | Djokic et al. | |
| 4,020,270 A | 4/1977 | Arcamone et al. | |
| 4,219,641 A | 8/1980 | Desposato et al. | |
| 4,328,334 A | 5/1982 | Kobrehel et al. | |
| 4,465,674 A | 8/1984 | Bright et al. | |
| 4,474,768 A | 10/1984 | Bright | |
| 4,512,982 A | 4/1985 | Hauske et al. | |
| 4,517,359 A | 5/1985 | Kobrehel et al. | |
| 4,518,590 A | 5/1985 | Hauske et al. | |
| 4,526,889 A | 7/1985 | Bright | |
| 4,963,531 A | 10/1990 | Remington | |
| 5,023,085 A | 6/1991 | Francoeur et al. | |
| 5,250,518 A | 10/1993 | Kobrehel et al. | |
| 5,332,807 A | 7/1994 | Waddell et al. | |
| 5,441,939 A | 8/1995 | Yang | |
| 5,605,889 A | 2/1997 | Curatolo et al. | |
| 5,674,911 A | 10/1997 | Emanuele et al. | |
| 5,686,587 A | 11/1997 | Yang | |
| 5,747,058 A | 5/1998 | Tipton et al. | |
| 5,760,010 A | 6/1998 | Klein | |
| 5,786,338 A | 7/1998 | Klein | |
| 5,795,871 A | 8/1998 | Narita et al. | |
| 5,811,088 A | 9/1998 | Hunter et al. | |
| 5,869,629 A | 2/1999 | Bayod Jasanada et al. | |
| 5,885,601 A | 3/1999 | Sokal | |
| 5,958,888 A | 9/1999 | Macy et al. | |
| 6,013,778 A | 1/2000 | Heggie et al. | |
| 6,025,350 A | 2/2000 | Masamune et al. | |
| 6,043,225 A | 3/2000 | Shor et al. | |
| 6,054,133 A | 4/2000 | Horwitz et al. | |
| 6,172,069 B1 | 1/2001 | Klimstra et al. | |
| 6,174,865 B1 | 1/2001 | Klein | |
| 6,218,368 B1 | 4/2001 | Wirostko | |
| 6,239,112 B1 | 5/2001 | Macy et al. | |
| 6,245,903 B1 | 6/2001 | Karimian et al. | |
| 6,268,489 B1 | 7/2001 | Allen et al. | |
| 6,281,199 B1 | 8/2001 | Gupta | |
| 6,339,063 B1 | 1/2002 | Kropp et al. | |
| 6,365,574 B2 * | 4/2002 | Singer et al. | 514/29 |
| 6,369,035 B1 | 4/2002 | Kobrehel et al. | |
| 6,383,471 B1 | 5/2002 | Chen et al. | |
| 6,407,074 B1 | 6/2002 | Bronk et al. | |
| 6,420,536 B1 | 7/2002 | Bronk et al. | |
| 6,420,537 B1 | 7/2002 | Bosch et al. | |
| 6,451,990 B1 | 9/2002 | Bayod Jasanada et al. | |
| 6,465,437 B1 | 10/2002 | Rafka et al. | |
| 6,500,987 B1 | 12/2002 | Schwartz et al. | |
| 6,504,017 B1 | 1/2003 | Bosch et al. | |
| 6,528,492 B1 | 3/2003 | de la Torre Garcia et al. | |
| 6,586,576 B2 | 7/2003 | Aronhime et al. | |
| 6,645,528 B1 | 11/2003 | Straub et al. | |
| 6,703,372 B1 | 3/2004 | Centellas et al. | |
| 6,720,001 B2 | 4/2004 | Chen et al. | |
| 6,723,341 B2 | 4/2004 | Rudnic et al. | |
| 6,761,895 B2 | 7/2004 | Sawada et al. | |
| 6,764,997 B2 | 7/2004 | Tenengauzer et al. | |
| 6,777,393 B2 | 8/2004 | Bronk et al. | |
| 6,825,327 B2 | 11/2004 | Sklavounos et al. | |
| 6,861,413 B2 | 3/2005 | Li et al. | |
| 2001/0014670 A1 | 8/2001 | Balin et al. | |
| 2001/0047089 A1 | 11/2001 | Aronhime et al. | |

(Continued)

FOREIGN PATENT DOCUMENTS

CA    1314876    3/1993

(Continued)

OTHER PUBLICATIONS

Ghandi et al., *Eur. J. Pharm. Sci.*, 16(3), 175-184 (2002).

(Continued)

*Primary Examiner*—Elli Peselev
(74) *Attorney, Agent, or Firm*—Leydig, Voit & Mayer, Ltd.

(57) ABSTRACT

The invention provides among other things a stable, sterile pharmaceutical formulation comprising lyophilized azithromycin and ethanol. The invention also provides a method of producing a stable, sterile pharmaceutical product comprising lyophilized azithromycin. The invention also provides a pharmaceutical dosage form comprising the pharmaceutical formulation, as well as a method of treating a disease in a patient comprising administering a solution of the pharmaceutical formulation to a patient.

17 Claims, No Drawings

U.S. PATENT DOCUMENTS

| | | |
|---|---|---|
| 2001/0048944 A1 | 12/2001 | Rudnic et al. |
| 2002/0007049 A1 | 1/2002 | Singer et al. |
| 2002/0012680 A1 | 1/2002 | Patel et al. |
| 2002/0022054 A1 | 2/2002 | Sawada et al. |
| 2002/0028920 A1 | 3/2002 | Lifshitz et al. |
| 2002/0044965 A1 | 4/2002 | Curatolo et al. |
| 2002/0049167 A1 | 4/2002 | Abraham et al. |
| 2002/0061858 A1 | 5/2002 | Bronk et al. |
| 2002/0071822 A1 | 6/2002 | Uhrich |
| 2002/0086867 A1 | 7/2002 | Dubois et al. |
| 2002/0107265 A1 | 8/2002 | Chen et al. |
| 2002/0111318 A1 | 8/2002 | Rengaraju |
| 2002/0115621 A1 | 8/2002 | Su et al. |
| 2002/0142050 A1 | 10/2002 | Straub et al. |
| 2002/0143211 A1 | 10/2002 | Dolitzky et al. |
| 2002/0156026 A1 | 10/2002 | Bronk et al. |
| 2003/0007958 A1 | 1/2003 | Chen |
| 2003/0018030 A1 | 1/2003 | Garti et al. |
| 2003/0050620 A1 | 3/2003 | Odidi et al. |
| 2003/0064939 A1 | 4/2003 | Sklavounos et al. |
| 2003/0092642 A1 | 5/2003 | Rafka et al. |
| 2003/0104055 A1 | 6/2003 | Rudnic et al. |
| 2003/0105066 A1 | 6/2003 | Soldato et al. |
| 2003/0108597 A1 | 6/2003 | Chancellor et al. |
| 2003/0119760 A1 | 6/2003 | Hussain et al. |
| 2003/0119865 A1 | 6/2003 | Dubois et al. |
| 2003/0139583 A1 | 7/2003 | Singh et al. |
| 2003/0143259 A1 | 7/2003 | Roy et al. |
| 2003/0148964 A1 | 8/2003 | Dunne |
| 2003/0162730 A1 | 8/2003 | Li et al. |
| 2003/0165563 A1 | 9/2003 | Murphy et al. |
| 2003/0176369 A1 | 9/2003 | Tenengauzer et al. |
| 2003/0190365 A1 | 10/2003 | Fergione et al. |
| 2003/0206951 A1 | 11/2003 | Rudnic et al. |
| 2003/0207819 A1 | 11/2003 | Moskowitz |
| 2003/0215496 A1 | 11/2003 | Patel et al. |
| 2003/0228357 A1 | 12/2003 | Johnson et al. |
| 2003/0228381 A1 | 12/2003 | Qazi et al. |
| 2004/0009930 A1 | 1/2004 | Su et al. |
| 2004/0014951 A1 | 1/2004 | Dumic et al. |
| 2004/0014952 A1 | 1/2004 | Rengaraju |
| 2004/0023896 A1 | 2/2004 | Bronk et al. |
| 2004/0023898 A1 | 2/2004 | Dunne |
| 2004/0033969 A1 | 2/2004 | Burnet et al. |
| 2004/0043944 A1 | 3/2004 | Li et al. |
| 2004/0043945 A1 | 3/2004 | Li et al. |
| 2004/0053862 A1 | 3/2004 | Centellas et al. |
| 2004/0082527 A1 | 4/2004 | Li et al. |
| 2004/0087517 A1 | 5/2004 | Burnet et al. |
| 2004/0087564 A1 | 5/2004 | Wright et al. |
| 2004/0091527 A1 | 5/2004 | Curatolo et al. |
| 2004/0092460 A1 | 5/2004 | Dumic et al. |
| 2004/0101557 A1 | 5/2004 | Gibson et al. |
| 2004/0109894 A1 | 6/2004 | Shefer et al. |
| 2004/0121966 A1 | 6/2004 | Li et al. |
| 2004/0132673 A1 | 7/2004 | Suh et al. |
| 2004/0138149 A1 | 7/2004 | Li et al. |
| 2004/0138150 A1 | 7/2004 | Santi et al. |
| 2004/0170617 A1 | 9/2004 | Finegold |
| 2004/0175426 A1 | 9/2004 | Ashton |
| 2004/0180842 A1 | 9/2004 | Bronk et al. |
| 2004/0192622 A1 | 9/2004 | Tenengauzer et al. |
| 2004/0197341 A1 | 10/2004 | Pechere et al. |
| 2004/0198675 A1 | 10/2004 | Sugamata |
| 2004/0209826 A1 | 10/2004 | Rafka et al. |
| 2004/0214752 A1 | 10/2004 | Britten et al. |
| 2004/0224023 A1 | 11/2004 | Hunter et al. |
| 2004/0226501 A1 | 11/2004 | Keri et al. |
| 2004/0226852 A1 | 11/2004 | Pesachovich et al. |
| 2004/0229955 A1 | 11/2004 | Andersen et al. |
| 2004/0247628 A1 | 12/2004 | Lintz et al. |
| 2004/0254127 A1 | 12/2004 | Emmerich et al. |
| 2004/0265984 A1 | 12/2004 | Yonath et al. |
| 2004/0266997 A1 | 12/2004 | Pesachovich et al. |
| 2005/0002865 A1 | 1/2005 | Klaveness et al. |
| 2005/0090459 A1 | 4/2005 | Li et al. |
| 2005/0106239 A1 | 5/2005 | Tenengauzer et al. |
| 2005/0209172 A1 | 9/2005 | Woo et al. |

FOREIGN PATENT DOCUMENTS

| | | |
|---|---|---|
| CN | 1093370 A | 10/1994 |
| CN | 1114960 A | 1/1996 |
| CN | 1123279 A | 5/1996 |
| CN | 1161971 A | 10/1997 |
| CN | 1205338 A | 1/1999 |
| EP | 0101186 A1 | 2/1984 |
| EP | 0284203 A2 | 9/1988 |
| EP | 0298650 B1 | 1/1989 |
| EP | 0307128 B1 | 3/1989 |
| EP | 0445743 B1 | 9/1991 |
| EP | 0467331 A1 | 1/1992 |
| EP | 0677530 B1 | 10/1995 |
| EP | 0827965 A2 | 6/1998 |
| EP | 0879823 B1 | 11/1998 |
| EP | 0941999 A2 | 9/1999 |
| EP | 1 103 558 B1 | 5/2001 |
| EP | 0984020 B1 | 7/2002 |
| EP | 1234833 A2 | 3/2003 |
| EP | 1103558 B1 | 6/2003 |
| EP | 1227102 B1 | 3/2004 |
| EP | 1400528 A1 | 3/2004 |
| EP | 1 514 877 A1 | 3/2005 |
| GB | 2395482 A | 5/2004 |
| JP | 01038096 A | 2/1989 |
| JP | 01193292 A | 8/1989 |
| JP | 02083326 A | 2/1990 |
| JP | 05132497 A | 5/1993 |
| JP | 06184186 A | 5/1994 |
| JP | 08041058 A | 2/1996 |
| JP | 10072482 A | 3/1998 |
| JP | 10316699 A | 12/1998 |
| JP | 41132276 A | 11/1999 |
| JP | 2001187797 A | 7/2000 |
| JP | 2000219697 A | 8/2000 |
| WO | WO 89/00576 A1 | 1/1989 |
| WO | WO 94/26758 A1 | 11/1994 |
| WO | WO 95/30422 A1 | 11/1995 |
| WO | WO 96/19489 A1 | 6/1996 |
| WO | WO 98/05674 A1 | 2/1998 |
| WO | WO 98/33482 A1 | 8/1998 |
| WO | WO 99/32500 A2 | 7/1999 |
| WO | WO 99/58541 A2 | 11/1999 |
| WO | WO 01/87912 A1 | 5/2000 |
| WO | WO 00/32203 A1 | 6/2000 |
| WO | WO 02/07736 A1 | 1/2002 |
| WO | WO 02/09640 A2 | 2/2002 |
| WO | WO 02/085898 A1 | 10/2002 |
| WO | WO 02/087596 A2 | 11/2002 |
| WO | WO 02/087596 A3 | 11/2002 |
| WO | WO 02/094843 A1 | 11/2002 |
| WO | WO 03/018031 A2 | 3/2003 |
| WO | WO 03/020290 A1 | 3/2003 |
| WO | WO 03/032922 A2 | 4/2003 |
| WO | WO 03/063838 A1 | 8/2003 |
| WO | WO 03/070254 A1 | 8/2003 |
| WO | WO 03/082889 A1 | 10/2003 |
| WO | WO 03/102009 A1 | 12/2003 |
| WO | WO 2004/000865 A1 | 12/2003 |
| WO | WO 2004/009608 A2 | 1/2004 |
| WO | WO 2004/035063 A1 | 4/2004 |

WO WO 2004/083227 A1 9/2004

OTHER PUBLICATIONS

Pfizer Labs, Division of Pfizer Inc., NY, NY 10017, "Zithromax," 70-5191-00-8 (Oct. 2003).

Pfizer Labs, Division of Pfizer Inc., NY, NY 10017, "Zithromax," 69-4763-00-7 (Oct. 2002).

Pfizer Labs, Division of Pfizer Inc., NY, NY 10017, "Zithromax," 70-5179-00-1 (Oct. 2002).

* cited by examiner

LYOPHILIZED AZITHROMYCIN FORMULATION

FIELD OF THE INVENTION

This invention pertains among other things to a lyophilized azithromycin formulation, solutions thereof, and methods of preparing and using lyophilized azithromycin.

BACKGROUND OF THE INVENTION

Azithromycin is a macrolide antibiotic which has the formula:

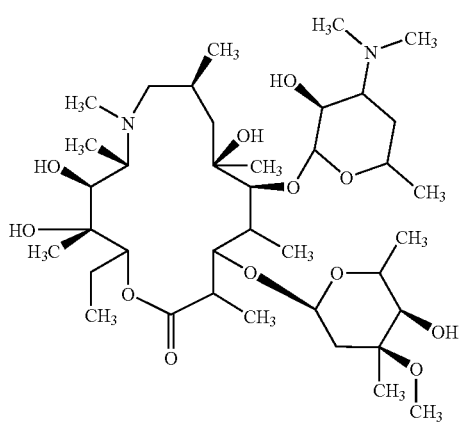

Azithromycin is chemically described as (2R,3S,4R,5R, 8R,10R,11R,12S,13S,14R)-13-[(2,6-dideoxy-3-O-methyl-α-L-ribo-hexo-pyranosyl)oxy]-2-ethyl-3,4,10-trihydroxy-3, 5,6,8,10,12,14-heptamethyl-11-[[3,4,6-trideoxy-3-(dimethylamino)-β-D-xylo-hexopyranosyl]oxy]-1-oxa-6-azacyclopentadecan-15-one. Azithromycin has the molecular formula $C_{38}H_{72}N_2O_{12}$, and has a molecular weight of 749.00.

Azithromycin is approved in the United States for the treatment of community-acquired pneumonia and pelvic inflammatory disease when caused by susceptible organisms, such as *Staphylococcus aureus, Streptococcus pneumoniae, Streptococcus agalactiae, Streptococcus pyogenes, Haemophilus ducreyi, Haemophilus influenzae, Moraxella catarrhalis, Neisseria gonorrhoeae, Chlamydia pneumoniae, Chlamydia trachomatis, Legionella pneumophila, Mycoplasma hominis,* and *Mycoplasma pneumoniae.*

Azithromycin is supplied in lyophilized form under vacuum in a 10-mL vial equivalent to 500 mg of azithromycin for intravenous administration (e.g., marketed by Pfizer under the trade name Zithromax®). Each vial also contains sodium hydroxide and citric acid. For therapeutic applications, the lyophilized azithromycin is reconstituted with a sterile aqueous vehicle such as Sterile Water for Injection, USP, and is administered by injection. Typically, the 500 mg dosage form is reconstituted with 4.8 mL of the aqueous vehicle to achieve a concentration of about 100 mg/nL. Solutions of azithromycin may be diluted further in injectable fluids such as Normal Saline (0.9% sodium chloride), ½ Normal Saline (0.45% sodium chloride), 5% Dextrose in Water, Lactated Ringer's Solution, 5% Dextrose in ½ Normal Saline with 20 mEq KCl, 5% Dextrose in Lactated Ringer's Solution, 5% Dextrose in ⅓ Normal Saline, 5% dextrose in ½ Normal Saline, Normosol®-M in 5% Dextrose, and Normosol®-R in 5% Dextrose.

Azithromycin is normally administered via intravenous (i.v.) injection at a dosage of 500 mg per day for one to two days. Intravenous therapy typically is followed by oral administration of azithromycin at a single daily dose of 500 mg or 250 mg, to complete a 7-10 day course of therapy. Reconstituted azithromycin solution is stable for 24 hours when stored below 30° C. or 86° F. When diluted to 1.0-2.0 mg/mL, azithromycin for injection is stable for 24 hours at or below room temperature (30° C. or 86° F.), or for 7 days if stored under refrigeration (5° C. or 41° F.).

Current approaches for manufacturing lyophilized forms of azithromycin utilize the dihydrate form of azithromycin (see, e.g., U.S. Pat. No. 6,268,489). There remains a need for a stable, sterile form of lyophilized azithromycin and for efficient methods of producing such a formulation. The invention provides such a formulation and methods. These and other advantages of the present invention, as well as additional inventive features, will be apparent from the description of the invention provided herein.

BRIEF SUMMARY OF THE INVENTION

The invention provides among other things a stable, sterile pharmaceutical formulation comprising lyophilized azithromycin and ethanol, wherein the ethanol is present in an amount of about 5% by weight or less, and preferably in an amount of from about 0.003% to about 3% by weight of the pharmaceutical formulation. The pharmaceutical formulation further optimally comprises citric acid (or other appropriate form of citrate) and/or sodium hydroxide. The invention provides a solution prepared by dissolving the pharmaceutical formulation in an aqueous vehicle. The invention also provides a liquid composition comprising an ethanolate of azithromycin, citric acid, and sodium hydroxide.

The invention also provides a method of producing a stable, sterile pharmaceutical product according to the invention comprising lyophilized azithromycin, which method comprises preparing a composition comprising an ethanolate of azithromycin, and lyophilizing the composition. In addition, the invention provides a method of producing a stable, sterile pharmaceutical formulation comprising lyophilized azithromycin, which method comprises (a) preparing a liquid composition comprising an ethanolate of azithromycin and an aqueous solvent, (b) chilling the composition to a temperature from about −10° C. to about 15° C., wherein the temperature is maintained for at least about 20 minutes to about 2 hours, (c) freezing the composition to a temperature of from about −10° C. to about −70° C., to produce a frozen mixture, wherein the temperature is maintained for at least about 30 minutes to about 20 hours, (d) subjecting the frozen mixture to a primary drying stage, which comprises applying a vacuum to reduce the pressure by an amount effective to remove aqueous solvent from the frozen mixture, and, while applying the vacuum, changing the temperature of the frozen mixture to a primary drying temperature, wherein the primary drying temperature is from about −30° C. to about 20° C., and wherein the primary drying temperature is maintained for at least about 15 hours to about 50 hours, to produce a first intermediate, and (e) subjecting the first intermediate to a secondary drying stage, which comprises applying a vacuum to reduce the pressure by an amount effective to remove aqueous solvent from the first intermediate, and, while applying the vacuum, (i) changing the temperature of the first intermediate to a first secondary drying temperature, wherein the first secondary drying temperature is from about 0° C. to about 45° C., and wherein the first secondary drying temperature is maintained for at least about 5 hours to about 30 hours, and (ii) changing the temperature of the first intermediate to a second secondary drying temperature, wherein the second secondary drying temperature is from about 0° C. to about 60° C., and wherein the second secondary drying temperature is maintained for at least about 5 hours to about 30 hours, to produce the pharmaceutical formulation. The inventive method optionally further can be carried out comprising a secondary drying stage which comprises changing the temperature of the intermediate to only the "second" secondary drying temperature (i.e., from about 0° C. to about 60° C.), and not including drying at a "first" secondary drying temperature.

The invention further provides a pharmaceutical dosage form comprising a sealed container and a pharmaceutical formulation comprising a therapeutically effective amount of lyophilized azithromycin and an amount of ethanol contained within the container, wherein the ethanol is present in an amount from about 0.003% to about 3.0% by weight of the pharmaceutical formulation. The pharmaceutical formulation further optimally comprises citric acid (or other appropriate form of citrate) and/or sodium hydroxide. Still further provided by the invention is a method of treating a disease in a patient, which method comprises dissolving the above-described pharmaceutical formulation in a pharmaceutically acceptable solvent to produce a pharmaceutically acceptable solution, and administering the solution to a patient in need thereof.

DETAILED DESCRIPTION OF THE INVENTION

The invention provides among other things a stable, sterile pharmaceutical formulation comprising lyophilized azithromycin and ethanol. The pharmaceutical formulation further optimally comprises citric acid (or other appropriate form of citrate) and/or sodium hydroxide. The lyophilized azithromycin of the present invention is a white to off-white powder of high purity. The lyophilized azithromycin of the present invention preferably has a purity of about 90% or greater (i.e., contains about 10% or less of total impurities based on the total weight of azithromycin), more preferably has a purity of about 96% or greater (i.e., contains about 4% or less of total impurities based on the total weight of azithromycin), and even more preferably has a purity of about 98% or greater (i.e., contains about 2% or less of total impurities based on the total weight of azithromycin). Most preferably, the lyophilized azithromycin has a purity of about 98%, about 98.5%, or about 99% (i.e., contains about 2%, about 1.5%, or about 1.0%, respectively, of total impurities based on the total weight of azithromycin). Purity can be determined by high performance liquid chromatography assay (e.g., allowing separation of pure lyophilized azithromycin from impurities, and quantitation of the relative amounts by the determination of the peak area of pure azithromycin as compared to total peak area), or by a similar method.

The lyophilized azithromycin formulation can comprise any suitable amount of azithromycin, but preferably comprises a therapeutically effective amount of azithromycin. A "therapeutically effective amount" means an amount sufficient to show a meaningful benefit in an individual, e.g., promoting at least one aspect of antimicrobial activity, or treatment, healing, prevention, or amelioration of other relevant medical condition(s) such as that associated with a particular microbial infection. Therapeutically effective amounts may vary depending upon the biological effect desired in the individual, condition to be treated, and the individual. In this regard, the lyophilized azithromycin preferably is present in the formulation in an amount from about 100 mg to about 1 gram (e.g., about 100 mg, about 300 mg, about 500 mg, about 700 mg, or about 1 gram). More preferably, the lyophilized azithromycin is present in an amount from about 300 mg to about 700 mg (e.g., about 300 mg, about 500 mg, or about 700 mg). Most preferably, the lyophilized azithromycin is present in an amount of about 500 mg. Optionally the azithromycin present in the lyophilized azithromycin formulation predominately is in the form of azithromycin citrate.

The lyophilized azithromycin formulation can be prepared using any suitable form of azithromycin, including salts, hydrates, or solvates thereof. In this regard, the lyophilized azithromycin formulation can be prepared using anhydrous azithromycin, or a hydrated form of azithromycin (e.g., a monohydrate or a dihydrate of azithromycin) (see, e.g., U.S. Pat. No. 6,268,489 and U.S. patent application Publication Nos. 2001/0047089 A1, 2003/0139583 A1, and 2003/0162730 A1). Alternatively and preferably, the lyophilized azithromycin formulation can be prepared using a solvate of a hydrate of azithromycin. More preferably, the lyophilized azithromycin formulation is prepared using an ethanolate of azithromycin, especially an ethanolate of azithromycin monohydrate (see, e.g., U.S. patent application Publication No. 2002/0007049 and PCT International Application WO 00/32203). Most preferably, the lyophilized azithromycin formulation is prepared using azithromycin monohydrate hemiethanolate.

In a preferred embodiment of the invention, the lyophilized azithromycin formulation has a low moisture content. The moisture content of the inventive lyophilized azithromycin formulation is the result of residual solvent that remains in the formulation after the lyophilization process. The moisture content can be the product of any suitable solvent that is used in the method of producing the lyophilized azithromycin formulation described herein. Suitable solvents include, for example, aqueous solvents (i.e., water), organic solvents, or a combination of an aqueous solvent and an organic solvent. Preferably, the lyophilized azithromycin formulation has a moisture content of less than from about 0.01 wt % to about 10 wt %, where the wt % is the % water relative to the dry weight of the lyophilized azithromycin formulation. More preferably the moisture content is less than from about 0.01 wt % to about 5 wt %, and even more preferably is less than from about 0.01 wt % to about 1.5 wt %. Most preferably, the moisture content is about 1.5 wt % or about 1 wt %, and even more desirably, is less than about 1 wt %.

As discussed herein, the inventive lyophilized azithromycin formulation preferably is prepared using a hemiethanolate of azithromycin monohydrate. Thus, in a preferred embodiment of the invention, the lyophilized azithromycin formulation comprises ethanol. The lyophilized azithromycin formulation can comprise any suitable amount of ethanol, especially ethanol in an amount of about 5% by weight or less of the pharmaceutical formulation. The lyophilized azithromycin formulation preferably comprises ethanol in an amount of from about 0.003% to about 3% by weight (wt %) of the pharmaceutical formulation, and more preferably comprises ethanol in an amount of from about 0.003% to about 1.5% by weight (wt %). Even more preferably, the lyophilized azithromycin formulation contains ethanol in an amount of from about 0.005% to about 0.5% by weight (e.g., from about 0.015 wt % to about 0.15 wt %) of the pharmaceutical formulation. Most preferably, the lyophilized azithromycin formulation contains about 0.03%, about 0.04%, about 0.05%, about 0.06%, about 0.07%, about 0.08%, about 0.09%, about 0.10%, about 0.11%, about 0.12%, or about 0.13% by weight of ethanol.

The lyophilized azithromycin formulation of the invention additionally optimally comprises citric acid (or other appropriate form of citrate) and/or sodium hydroxide. These components are further described below in the context of the liquid composition. The "liquid composition" is the formulation of the invention prior to lyophilization (e.g., the pre-lyophilization solution). In some instances, however, it may be desirable to prepare a pharmaceutical azithromycin formulation as a liquid rather than in a lyophilized form. Along these lines, a pharmaceutical formulation according to the invention comprises azithromycin and ethanol (as well as further optional components) preferably either in lyophilized form, or as a liquid. For the liquid compositions of the invention to serve as pharmaceutical azithromycin formulations, optionally additional components are included, such as preservatives (e.g., methylparaben and propylparaben), stabilizers (e.g., sugars), and buffering agents (e.g., sodium citrate, sodium hydroxide, sodium acetate, and others).

In terms of the lyophilized azithromycin formulation, preferably the formulation further comprises citric acid. Citric acid desirably is employed in the form of its monohydrate, or can be used as any other appropriate form of citrate, e.g., anhydrous, in the form of sodium citrate, etc. Citric acid (or other appropriate form of citrate) preferably is included in the lyophilized azithromycin formulation in an amount of from about 100 mg to about 1 gram (e.g., about 100 mg, about 300 mg, about 500 mg, about 700 mg, or about 1 gram). More preferably the lyophilized azithromycin formulation comprises citric acid (or other appropriate form of citrate) in an amount of from about 300 mg to about 700 mg (e.g., about 300 mg, about 500 mg, or about 700 mg). Most preferably, the lyophilized azithromycin formulation comprises an amount of from about 410 mg to about 420 mg (especially about 414 mg) of citric acid, or an amount of from about 450 mg to about 460 mg (especially about 452 mg) of citric acid monohydrate. Optionally, citric acid can be replaced in the lyophilized azithromycin formulation with the functionally equivalent amount of any appropriate acid (e.g., hydrochloric acid, lactic acid, glycolic acid, acetic acid, phosphoric acid, tartaric acid, or other acid). According to the invention, a "functionally equivalent amount" of acid is the amount of the appropriate acid that is able to generate the same acidity as if citric acid monohydrate were employed.

The lyophilized azithromycin formulation preferably further comprises from about 100 mg to about 500 mg (e.g., about 100 mg, about 200 mg, about 300 mg, about 400 mg, or about 500) of sodium hydroxide. More preferably, the lyophilized azithromycin formulation comprises from about 150 mg to about 250 mg (e.g., about 150 mg, about 200 mg, or about 250 mg) of sodium hydroxide. Most preferably, the lyophilized azithromycin formulation comprises from about 197 mg to about 204 mg of sodium hydroxide. Optionally, sodium hydroxide can be replaced in the lyophilized azithromycin formulation with the functionally equivalent amount of any appropriate base (e.g., potassium hydroxide, calcium hydroxide, aluminum hydroxide, zinc hydroxide, or other base). According to the invention, a "functionally equivalent amount" of base is the amount of the appropriate base that is able to generate the same basicity as if sodium hydroxide were employed.

The inventive lyophilized azithromycin formulation (or the liquid pharmaceutical azithromycin formulation) according to the invention can be contained within a sealed container. Preferably, each azithromycin formulation (e.g., the lyophilized or the liquid formulation) is contained within a container that is sealed aseptically. More preferably, the container is provided with an opening and a means for aseptically sealing the opening, e.g., such that the sealed container is fluidly sealed or the sealed opening is substantially impermeable to atmospheric gasses, moisture, pathogenic microorganisms, or the like. The container can be constructed of any suitable material such as, for example, glass, polypropylene, Daikyo Resin CZ (sold by Daikyo Gomu Seiko, Ltd.), polyethylene terephthalate, and the like. In a preferred embodiment, the container is constructed of glass. Suitable glass containers include, but are not limited to, glass vials. Suitable glass vials include molded and tubing glass vials such as, for example, Type I molded glass vials, and the like. Such molded and tubing glass vials can be obtained from Kimble Glass, Inc., Vineland, N.J., Wheaton Science Products, Millville, N.J., or other companies.

A suitable means for sealing the container can include, for example, a stopper, a cap, a lid, a closure, a covering which fluidly seals the container, or the like. Examples of suitable closures include closures that are suitable for medical vials, such as those described in U.S. Pat. No. 4,671,331, and references cited therein. The means for sealing the container are not limited to separate closures or closure devices, but also includes self-sealing containers and containers which are manufactured and sealed during filling operations. In a preferred embodiment, the means for aseptically sealing the container includes a stopper such as, for example, a stopper that is configured to fluidly seal the opening. Suitable stoppers include conventional medical grade stoppers which do not degrade or release significant amounts of impurities upon exposure to the constituted aqueous azithromycin solution. Preferably, the stopper is constructed of an elastomer, which is more preferably an elastomer that is pierceable by a hypodermic needle or a blunt cannula. Exemplary stoppers include 6720 GC gray rubber stoppers from American Stelmi Corporation, 4432/50 gray rubber stoppers from West Company, and the like.

Optionally, an outer seal is provided which covers and entirely surrounds the stopper. The outer seal can be constructed of any suitable material. When an outer seal is used, it is preferably fitted with a lid that can be easily manually removed to provide access to the stopper. Suitable outer seals can include, for example, Flip-off Aluminum/Polypropylene Seals (lacquered or non-lacquered aluminum), marketed by The West Company, Inc., and other manufacturers. Such seals include an outer rim made of a suitable material, such as aluminum, that entirely surrounds the lateral edge of the stopper and further include a lid (typically polypropylene or other suitable material) that entirely covers the upper surface of the stopper. The polypropylene lid can be "flipped" off e.g., by exerting upward pressure with a finger or thumb, to provide access to the stopper, e.g., so that it can be punctured with a hypodermic needle to deliver an aqueous vehicle for constitution (see, e.g., U.S. Pat. No. 6,136,814).

Preferably, the container contains a therapeutically effective dose of azithromycin (e.g., in the lyophilized azithromycin formulation or in the liquid pharmaceutical azithromycin formulation) and is of sufficient volume (i.e., has sufficient capacity) to contain the volume of solution that is recommended for constitution of the lyophilized azithromycin formulation. More preferably, the container contains azithromycin in an amount which is an approved dosage for treating microbial infections, such as those described herein, and is of sufficient volume (i.e., has sufficient capacity) to contain the total volume of solution recommended for constitution. In a particularly preferred embodiment, the container volume (i.e., container capacity) is about 10 mL, and an amount of the inventive lyophilized azithromycin formulation equivalent to about 500 mg azithromycin is contained within the container.

The invention further provides a solution prepared by dissolving the inventive lyophilized azithromycin formulation in an aqueous vehicle. The aqueous vehicle is preferably a sterile aqueous vehicle that is normally used as liquid vehicle for injection. Suitable aqueous vehicles include, for example, sterile water (e.g., Sterile Water for Injection, USP), sodium chloride solutions (e.g., 0.9% Sodium Chloride for Injection, USP), dextrose solutions (e.g., 10% Dextrose for Injection), sodium chloride/dextrose mixtures (e.g., 5% Dextrose and 0.225% Sodium Chloride for Injection, 5% Dextrose and 0.45% Sodium Chloride for Injection), Lactated Ringer's for Injection, and mixtures thereof. Optionally, the lyophilized azithromycin formulation is first reconstituted (e.g., with sterile water) and then further diluted (e.g., with a sodium chloride solution).

The inventive lyophilized azithromycin formulation can be dissolved in any suitable volume of the aqueous vehicle. Preferably, the lyophilized azithromycin is dissolved in about 10 mL or less (e.g., about 10 mL, about 8 mL, about 6 mL, about 4 mL, or about 1 mL) of the aqueous vehicle. Preferably, the lyophilized azithromycin is dissolved such that the concentration of azithromycin in the solution is about 100 mg/mL or less (e.g., about 90 mg/mL, about 70 mg/mL, about 50 mg/mL, about 30 mg/mL, or about 10 mg/mL). Most preferably, the lyophilized azithromycin is dissolved in about 5 mL of the aqueous vehicle, such that the concentration of azithromycin in the solution is about 100 mg/mL.

The solution prepared by dissolving the inventive lyophilized azithromycin formulation in an aqueous vehicle can be diluted further prior to administration to a patient. In this regard, the solution can be diluted in a suitable aqueous vehicle, such as those described herein. Preferably, the inventive solution is diluted in about 500 mL or less (e.g., about 500 mL, about 400 mL, about 300 mL, about 200 mL, or about 100 mL) of the aqueous vehicle. Preferably the inventive solution is diluted in the aqueous vehicle such that the final concentration of azithromycin in the diluted solution is about 2.0 mg/mL or less (e.g., about 1.0 mg/mL, about 0.5 mg/mL, about 0.2 mg/mL, or about 0.1 mg/mL). More preferably, the inventive solution is diluted in the aqueous vehicle such that the final concentration of azithromycin in the diluted solution is from about 0.5 mg/mL to about 5 mg/mL. Most preferably, the solution is diluted in about 250 mL to about 500 mL of the aqueous vehicle, such that the final concentration of azithromycin in the diluted solution is from about 2.0 mg/mL to about 1.0 mg/mL, respectively.

As described above, the invention also provides a liquid composition comprising an ethanolate of azithromycin, and which further optimally comprises citric acid (or other appropriate form of citrate) and/or sodium hydroxide. Preferably, the liquid composition comprises an ethanolate of a hydrated form of azithromycin (e.g., a monohydrate or a dihydrate). More preferably, the liquid composition comprises an ethanolate of azithromycin monohydrate. Most preferably, the liquid composition comprises a hemiethanolate of azithromycin monohydrate. The liquid composition can comprise any suitable amount of the ethanolate of azithromycin. In a particularly preferred embodiment of the invention, the azithromycin is present in the liquid composition in an amount from about 10 mg/mL to about 500 mg/mL (e.g., from about 10 mg/mL to about 300 mg/mL, from about 25 mg/mL to about 250 mg/mL, from about 50 mg/mL to about 100 mg/mL, or from about 60 mg/mL to about 90 mg/mL). Most preferably, the azithromycin in the liquid composition is present in an amount of about 70 mg/mL, about 71 mg/mL, about 72 mg/mL, about 73 mg/mL, about 74 mg/mL, about 75 mg/mL, about 76 mg/mL, about 77 mg/mL, about 78 mg/mL, about 79 mg/mL, or about 80 mg/mL, and especially in an amount of about 74 mg/mL or about 75 mg/mL.

The liquid composition preferably further comprises citric acid (or other appropriate form of citrate) and/or sodium hydroxide. Citric acid desirably is employed in the form of its monohydrate, or can be used as any other appropriate form of citrate, e.g., anhydrous, in the form of sodium citrate or the like. The liquid composition can contain any suitable amount of citric acid monohydrate required to buffer the inventive liquid composition. Preferably, the citric acid monohydrate is present in the liquid composition in an amount from about 5 mg/mL to about 500 mg/mL (e.g., from about 10 mg/mL to about 300 mg/mL, from about 25 mg/mL to about 250 mg/mL, from about 40 mg/mL to about 80 mg/mL, or from about 55 mg/mL to about 75 mg/mL). Most preferably, the citric acid monohydrate is present in the liquid composition in an amount of about 58 mg/mL, about 59 mg/mL, about 60 mg/mL, about 61 mg/mL, about 62 mg/mL, about 63 mg/mL, about 64 mg/mL, about 65 mg/mL, about 66 mg/mL, about 67 mg/mL, or about 68 mg/mL, and especially in an amount of about 62 mg/mL or about 63 mg/mL. One of ordinary skill easily can adjust these amounts in the case where a form other than citric acid monohydrate is employed. One of ordinary skill in the art also easily can adjust these amounts in the case where citric acid is replaced in the liquid composition with the functionally equivalent amount of any appropriate acid (e.g., hydrochloric acid, lactic acid, glycolic acid, acetic acid, phosphoric acid, tartaric acid, or other acid).

In addition, the liquid composition may contain a suitable amount of sodium hydroxide, such that the liquid composition achieves a desired pH. In this regard, the sodium hydroxide preferably is present in the liquid composition in an amount of from about 1 mg/mL to about 200 mg/mL (e.g., from about 1 mg/mL to about 100 mg/mL, from about 5 mg/mL to about 80 mg/mL, from about 10 mg/mL to about 50 mg/mL, or from about 20 mg/mL to about 40 mg/mL). Most preferably, the sodium hydroxide is present in the liquid composition in an amount of about 23 mg/mL, about 24 mg/mL, about 25 mg/mL, about 26 mg/mL, about 27 mg/mL, about 28 mg/mL, about 29 mg/mL, about 30 mg/mL, about 31 mg/mL, about 32 mg/mL, or about 33 mg/mL, and especially in an amount of about 27 mg/mL or about 28 mg/mL. Furthermore, rather than sodium hydroxide, any suitable alkali salt or appropriate base can be employed, e.g., potassium hydroxide, calcium hydroxide, aluminum hydroxide, zinc hydroxide, and the like.

The liquid composition further comprises a suitable solvent. Suitable solvents include, for example, aqueous solvents (i.e., water), organic solvents, or a combination of an aqueous solvent and an organic solvent. Preferably, the solvent comprises Water for Injection, USP.

The inventive liquid composition can further comprise excipients that are routinely employed in pharmaceutical formulations (e.g., pharmaceutical lyophilization formulations or pharmaceutical liquid formulations). Such excipients include, for example, buffering agents, surfactants, cryoprotectants, and bulking agents. Mannitol, for example, typically is used in the art as an excipient in lyophilization formulations. However, other suitable excipients can be included, which preferably do not deleteriously impact the properties of the inventive liquid composition. Examples of such excipients (e.g., buffering agents) include sodium or potassium phosphate, citric acid, lactic acid, tartaric acid, gelatin, glycine, and carbohydrates such as lactose, maltose, dextrose, dextran, hetastarch, etc. Additionally, any of the aforementioned buffering agents optionally can be used instead of citric acid. The excipients can be used alone or in combination, e.g., to provide a cake of good quality which readily disperses in an aqueous vehicle upon reconstitution.

The invention provides a method of producing a stable, sterile pharmaceutical product according to the invention comprising lyophilized azithromycin, which method comprises preparing a composition comprising an ethanolate of azithromycin, and lyophilizing the composition. Specifically, the method comprises (a) preparing a liquid composition comprising an ethanolate of azithromycin and an aqueous solvent, (b) chilling the composition to a temperature from about −10° C. to about 15° C., wherein the temperature is maintained for at least about 20 minutes to about 2 hours, (c) freezing the composition to a temperature of from about −10° C. to about −70° C., to produce a frozen mixture, wherein the temperature is maintained for at least about 30 minutes to about 20 hours, (d) subjecting the frozen mixture to a primary drying stage, which comprises applying a vacuum to reduce the pressure by an amount effective to remove aqueous solvent from the frozen mixture, and, while applying the vacuum, changing (e.g., raising or lowering) the temperature of the frozen mixture to a primary drying temperature, wherein the primary drying temperature is from about −30° C. to about 20° C., and wherein the primary drying temperature is maintained for at least about 15 hours to about 50 hours, to produce a first intermediate, and (e) subjecting the first intermediate to a secondary drying stage, which comprises applying a vacuum to reduce the pressure by an amount effective to remove aqueous solvent from the first intermediate, and, while applying the vacuum, (i) changing (e.g., raising or lowering) the temperature of the first intermediate to a first secondary drying temperature, wherein the first secondary drying temperature is from about 0° C. to about 45° C., and wherein the first secondary drying temperature is maintained for at least about 5 hours to about 30 hours, and (ii) changing (e.g., raising or lowering) the temperature of the first intermediate to a second secondary drying temperature, wherein the second secondary drying temperature is from about 0° C. to about 60° C., and wherein the second secondary drying temperature is maintained for at least about 5 hours to about 30 hours, to produce the pharmaceutical formulation. Descriptions of the lyophilized azithromycin, and components thereof, set forth above in connection with the inventive pharmaceutical formulation, also are applicable to those same aspects of the inventive method.

The composition is "chilled" or cooled to a temperature that does not freeze the aqueous solvent. Preferably, the liquid composition is chilled to a temperature of about 15° C. or lower (e.g., from about 5° C. to about 15° C., from about 0° C. to about 10° C., from about −10° C. to about 0° C., or from about −10° C. to about 15° C.). More preferably, the liquid composition is chilled to a temperature of about 10° C. or lower (e.g., from about 0° C. to about 10° C., from about −10° C. to about 0° C., or from about −15° C. to about 0° C.). Most preferably, the liquid composition is chilled to a temperature of about 5° C.

The temperature at which the composition is chilled can be maintained for any suitable length of time. Preferably, the temperature at which the composition is chilled is maintained for at least about 20 minutes to about 10 hours (e.g., about 30 minutes, about 1 hour, about 5 hours, about 7 hours, or about 9 hours). More preferably, the temperature at which the composition is chilled is maintained for at least about 20 minutes to about 2 hours (e.g., about 30 minutes, about 1 hour, about 90 minutes, or about 2 hours). Most preferably, the temperature at which the composition is chilled is maintained for at least about 1 hour.

The composition is "frozen" or cooled to a temperature that freezes the aqueous solvent. Preferably, the liquid composition is frozen sufficiently to allow for its removal under reduced pressure (e.g., by sublimation). Desirably, the liquid composition is frozen to a temperature of about −10° C. or lower (e.g., from about −10° C. to about −70° C., from about −20° C. to about −70° C., from about −30° C. to about −70° C., or from about −30° C. to about −60° C.), but is preferably frozen to a temperature of about −20° C. or lower (e.g., from about −30° C. to about −60° C.). More preferably, the liquid composition is frozen to a temperature of about −30° C. or lower (e.g., from about −30° C. to about −50° C.). Most preferably, the liquid composition is frozen to a temperature of about −40° C.

The composition can be frozen rapidly (e.g., by contacting a container of the solution in a cooling bath), or by cooling in stages (e.g., by lowering the temperature incrementally at progressively lower temperatures until the frozen mixture is obtained). Alternatively, the liquid composition can be frozen by continuously cooling at a substantially constant rate until the frozen mixture is obtained. For example, the composition can be frozen by cooling at a substantially constant rate of about 5° C. per minute or less (e.g., from about 0.1-5° C. per minute), at a rate of about 3° C. per minute or less (e.g., from about 0.1-3° C. per minute), at a rate of about 2° C. per minute or less (e.g., from about 0.1-2° C. per minute), or at a rate of about 1° C. per minute or less (e.g., from about 0.2-1° C. per minute, or from about 0.2-0.5° C. per minute), until the frozen mixture is obtained. Most preferably, the composition is frozen by cooling at a rate of about 0.2° C. per minute. Alternatively, the composition can be frozen using a combination of incremental cooling stages and one or more continuous cooling cycles (e.g., continuously cooling at a substantially constant rate) until the frozen mixture is obtained.

The temperature at which the composition is frozen can be maintained for any suitable length of time. Preferably, the temperature at which the composition is frozen is maintained for at least about 30 minutes to about 30 hours (e.g., about 1 hour, about 4 hours, about 10 hours, about 15 hours, or about 30 hours). More preferably, the temperature at which the composition is frozen is maintained for at least about 2 hours to about 15 hours (e.g., about 2 hours, about 4 hours, about 10 hours, or about 15 hours). Most preferably, the temperature at which the composition is frozen is maintained for at least about 4 hours.

The primary drying temperature is preferably from about −30° C. to about 35° C., but is more preferably from about −30° C. to about 20° C., and is even more preferably from about −10° C. to about 20° C. Most preferably, the primary drying temperature is from about 0° C. to about 20° C. (e.g., about 8° C.). In the primary drying stage, the temperature of the frozen composition can be changed in stages (e.g., raised incrementally at progressively higher temperatures until the primary drying temperature is attained, or lowered incrementally at progressively lower temperatures until the primary drying temperature is attained). Alternatively, the temperature of the frozen composition in the primary drying stage can be changed continuously (e.g., raised or lowered at a substantially constant rate) until the primary drying temperature is attained. It is particularly preferred according to the invention that the temperature of the frozen composition is changed to that of the primary drying temperature by raising the temperature. Preferably, the temperature of the frozen composition in the primary drying stage is changed at a rate of about 5° C. per minute or less (e.g., from about 0.05-2° C. per minute). More preferably, the temperature of the frozen composition in the primary drying stage is changed at a rate of about 3° C. per minute or less (e.g., from about 0.05-3° C. per minute). Still more preferably, the temperature of the frozen composition in the primary drying stage is changed at a rate of about 2° C. per minute or less (e.g., from about 0.1-2° C. per minute). Most preferably, the temperature of the frozen composition in the primary drying stage is changed at a rate of about 1° C. per minute or less (e.g., from about 0.1-1° C. per minute, or from about 0.1-0.5° C. per minute). In a particularly preferred embodiment, the temperature of the frozen composition in the primary drying stage is changed at a rate of about 0.5° C. per minute or less (e.g., about 0.5° C. per minute, about 0.2° C. per minute, or about 0.1° C. per minute).

The primary drying temperature in the primary drying stage is preferably maintained (e.g., held at a substantially constant temperature or kept within a particular range) until substantially all of the aqueous solvent is removed. In this regard, the primary drying temperature desirably is maintained for at least about 20 hours to about 80 hours (e.g., about 20 hours, about 40 hours, about 60 hours, about 70 hours, or about 80 hours). Preferably, the primary drying temperature is maintained for at least about 20 hours to about 40 hours (e.g., about 20 hours, about 30 hours, or about 40 hours). Most preferably, the primary drying temperature is maintained for at least about 30 hours to about 40 hours (e.g., about 36 hours). The removal of substantially all of the aqueous solvent can be determined by visual inspection. Alternatively, the removal of substantially all of the aqueous solvent can be determined on the basis of when the increase in the temperature of the frozen mixture (internal temperature) becomes insignificant. Normally, as the temperature is raised during the primary drying stage, the internal temperature "lags" behind (i.e., is lower than) the external temperature (sometimes referred to as the "shelf temperature"). In some instances when the external temperature is raised during the primary drying stage, the internal temperature can lag behind the external temperature by as much as about 10° C., or even more. Typically, the removal of substantially all of the solvent can be determined by comparing the internal temperature with the external temperature. The temperature of the frozen mixture and the external temperature can be measured using any suitable means, e.g., a thermometer, a thermocouple, or the like. In most instances, substantially all of the aqueous solvent is removed when the internal temperature remains steady or is about equal to (e.g., is slightly less than, is equal to, or slightly exceeds) the external temperature. In a preferred embodiment, the primary drying temperature is maintained until the temperature of the frozen mixture is about equal to the primary drying temperature.

The primary drying stage is preferably carried out at a pressure of about 500 micron Hg (67 Pascal (Pa)) or less (e.g., from about 10-500 micron Hg (1-67 Pa)), but is more preferably carried out at a pressure of about 200 micron Hg (27 Pa) or less (e.g., from about 10-200 micron Hg (1-27 Pa)). Most preferably, the primary drying stage is carried out at a pressure of about 150 micron Hg (20 Pa) or less (e.g., from about 10-150 micron Hg (1-20 Pa)). In a particularly preferred embodiment, the primary drying stage is carried out at a pressure of about 80 micron Hg (11 Pa).

The inventive method comprises a secondary drying stage, which comprises changing (e.g., raising or lowering) the temperature of the intermediate to that of a first secondary drying temperature and a second secondary drying temperature. The first secondary drying temperature in the secondary drying stage can range from about 0° C. to about 45° C., but is preferably from about 10° C. to about 40° C. More preferably, the first secondary drying temperature is about ambient temperature (e.g., from about 15° C. to about 35° C.), and is most preferably from about 20-40° C., (e.g., about 35° C.). Even more preferably, the first secondary drying temperature is from about 30° C. to about 50° C., and is most preferably from about 40° C. to about 50° C. (e.g., about 45° C.). The second secondary drying temperature in the secondary drying stage can range from about 0° C. to about 60° C., but is preferably from about 20° C. to about 50° C. The inventive method optionally further can be carried out comprising a secondary drying stage which comprises changing (e.g., raising or lowering) the temperature of the intermediate to that of the "second" secondary drying temperature (i.e., from about 0° C. to about 60° C.), and not including drying at a "first" secondary drying temperature. In the secondary drying stage, the temperature of the intermediate can be changed (e.g., raised or lowered) at a rate which is the same or different than the rate at which the temperature is changed (e.g., raised or lowered) in the primary drying stage. For example, the temperature of the intermediate in the secondary drying stage can be changed in stages (e.g., raised incrementally at progressively higher temperatures until the secondary drying temperature is attained, or lowered incrementally at progressively lower temperatures until the secondary drying temperature is attained). It is particularly preferred according to the invention that changing the temperature of the intermediate to that of the secondary drying temperature (e.g., first secondary drying temperature and/or second secondary drying temperature) is done by raising the temperature. Alternatively, the temperature of the intermediate in the secondary drying stage can be changed continuously (e.g., raised or lowered at a substantially constant rate) until the secondary drying temperature is attained. Preferably, the temperature of the intermediate in the secondary drying stage is changed at a rate of about 5° C. per minute or less (e.g., from about 0.05-5° C. per minute). More preferably, the temperature of the intermediate in the secondary drying stage is changed at a rate of about 3° C. per minute or less (e.g., from about 0.05-3° C. per minute). Still more preferably, the temperature of the intermediate in the secondary drying stage is changed at a rate of about 2° C. per minute or less (e.g., from about 0.05-2° C. per minute). Most preferably, the temperature of the intermediate in the secondary drying stage is changed at a rate of about 1° C. per minute or less (e.g., from about 0.05-1° C. per minute, from about 0.1-0.5° C. per minute, or from about 0.05-0.1° C. per minute). In a particularly preferred embodiment, the first secondary drying temperature of the intermediate is changed at a rate of about 0.05° C. per minute, and the second secondary drying temperature of the intermediate is changed at a rate of about 0.1° C. per minute.

Preferably, the first and second secondary drying temperatures in the secondary drying stage are maintained until the moisture content of the lyophilized azithromycin formulation is less than about 5 wt % (% water relative to the dry weight of the lyophilized azithromycin formulation). More preferably, the first and second secondary drying temperatures in the secondary drying stage are held until the moisture content is about 3 wt % or less (% water relative to the dry weight of the lyophilized azithromycin formulation). Most preferably, the first and second secondary drying temperatures in the secondary drying stage are held until the moisture content is about 1 wt % (% water relative to the dry weight of the lyophilized azithromycin formulation). In this regard, the first secondary drying temperature preferably is maintained for at least about 5 hours to about 30 hours (e.g., about 5 hours, about 15 hours, about 25 hours, or about 30 hours). More preferably, the first secondary dying temperature is maintained for at least about 10 hours to about 20 hours (e.g., about 10 hours, about 12 hours, about 15 hours, or about 19 hours).

Most preferably, the first secondary drying temperature is maintained for at least about 15 hours. The second secondary drying temperature also preferably is maintained for at least about 5 hours to about 30 hours (e.g., about 5 hours, about 15 hours, about 25 hours, or about 30 hours). More preferably, the second secondary dying temperature is maintained for at least about 10 hours to about 20 hours (e.g., about 10 hours, about 12 hours, about 15 hours, or about 18 hours). Most preferably, the second secondary drying temperature is maintained for at least about 18 hours.

The secondary drying stage can be carried out at a pressure which is the same or different than the pressure at which the primary drying stage is carried out. Preferably, the secondary drying stage is carried out at a pressure of about 500 micron Hg (67 Pa) or less (e.g., from about 10-500 micron Hg (1-67 Pa)), but is more preferably carried out at a pressure of about 200 micron Hg (27 Pa) or less (e.g., from about 10-200 micron Hg (1-27 Pa)). Most preferably, the primary drying stage is carried out at a pressure of about 150 micron Hg (20 Pa) or less (e.g., from about 10-150 micron Hg (1-20 Pa)). In a particularly preferred embodiment, the secondary drying stage is carried out at a pressure of about 80 micron Hg (11 Pa).

In a preferred embodiment of the inventive method, the liquid composition comprising an ethanolate of azithromycin and an aqueous solvent is aseptically filtered and aseptically filled into a container before the liquid composition is chilled, frozen, and dried as described above. In this regard, the liquid composition preferably is filtered through a 0.45 μm prefilter. The liquid composition preferably is then filtered through two sterile 0.22 μm final filters in a clean, sterile receiving carboy. Glass vials are aseptically filled with the filtered composition and partially stoppered, and the resulting composition preferably is lyophilized in accordance with steps (b)-(e) of the inventive method described above.

The invention further provides a pharmaceutical dosage form comprising a sealed container and a pharmaceutical formulation comprising a therapeutically effective amount of lyophilized azithromycin and an amount of ethanol contained within the container, wherein the ethanol is present in an amount of about 5% by weight or less of the pharmaceutical formulation, and especially wherein the ethanol is present in an amount of from about 0.003% to about 3.0% by weight of the pharmaceutical formulation. Descriptions of the lyophilized azithromycin, and components thereof, set forth above in connection with the inventive pharmaceutical formulation, also are applicable to those same aspects of the inventive pharmaceutical dosage form. The pharmaceutical dosage form can be a sterile single-dose or sterile multiple-dose dosage form. Exemplary pharmaceutical dosage forms include a pharmaceutical dosage form comprising a sealed container (e.g., a container as described herein) and the inventive pharmaceutical formulation comprising a therapeutically effective amount of lyophilized azithromycin contained within the container. The inventive pharmaceutical dosage form preferably includes a dose of lyophilized azithromycin of about 100 mg to about 1 gram (e.g., about 100 mg, about 300 mg, about 500 mg, about 700 mg, or about 1 gram) contained within the container. More preferably, the pharmaceutical dosage form includes a dose of the lyophilized azithromycin of about 300 mg to about 700 mg (e.g., about 300 mg, about 500 mg, or about 700 mg). Most preferably, the pharmaceutical dosage form includes a dose of the lyophilized azithromycin of about 500 mg. Optionally the pharmaceutical dosage form further comprises citric acid monohydrate and sodium hydroxide.

The pharmaceutical formulation contained within the container can comprise any suitable amount of ethanol, especially an amount of ethanol of about 5% by weight or less of the pharmaceutical formulation. The pharmaceutical formulation contained within the container preferably comprises ethanol in an amount of from about 0.003% to about 3% by weight (wt %) of the pharmaceutical formulation, and more preferably comprises ethanol in an amount of from about 0.003% to about 1.5% by weight (wt %). Even more preferably, the pharmaceutical formulation contains ethanol in an amount of from about 0.005% to about 0.5% by weight (e.g., from about 0.015 wt % to about 0.15 wt %) of the pharmaceutical formulation. Most preferably, the lyophilized azithromycin formulation contains about 0.03%, about 0.04%, about 0.05%, about 0.06%, about 0.07%, about 0.08%, about 0.09%, about 0.10%, about 0.11%, about 0.12%, or about 0.13% by weight of ethanol.

The inventive pharmaceutical dosage form preferably includes citric acid (or other appropriate form of citrate) in an amount of from about 100 mg to about 1 gram (e.g., about 100 mg, about 300 mg, about 500 mg, about 700 mg, or about 1 gram). More preferably the pharmaceutical dosage form comprises citric acid (or other appropriate form of citrate) in an amount of from about 300 mg to about 700 mg (e.g., about 300 mg, about 500 mg, or about 700 mg). Most preferably, the pharmaceutical dosage form comprises an amount of from about 410 mg to about 420 mg (especially about 414 mg) of citric acid, or an amount of from about 450 mg to about 460 mg (especially about 452 mg) of citric acid monohydrate. Optionally, citric acid can be replaced in the pharmaceutical dosage form with the functionally equivalent amount of any appropriate acid (e.g., hydrochloric acid, lactic acid, glycolic acid, acetic acid, phosphoric acid, tartaric acid, or other acid).

The pharmaceutical dosage form preferably further comprises from about 100 mg to about 500 mg (e.g., about 100 mg, about 200 mg, about 300 mg, about 400 mg, or about 500) of sodium hydroxide. More preferably, the pharmaceutical dosage form comprises from about 150 mg to about 250 mg (e.g., about 150 mg, about 200 mg, or about 250 mg) of sodium hydroxide. Most preferably, the pharmaceutical dosage form comprises from about 197 mg to about 204 mg of sodium hydroxide. Optionally, sodium hydroxide can be replaced in the lyophilized azithromycin formulation with the functionally equivalent amount of any appropriate base (e.g., potassium hydroxide, calcium hydroxide, aluminum hydroxide, zinc hydroxide, or other base).

To prepare the pharmaceutical dosage form, the pharmaceutical formulation can be packaged in the container by any suitable method known in the art. In a preferred embodiment of the invention, the inventive pharmaceutical formulation is packaged in the container by a method comprising the steps of (a) filling one or more containers with a liquid composition comprising a therapeutically effective amount of azithromycin and an aqueous solvent, each container defining an opening, (b) subjecting the composition in the one or more containers to the lyophilized azithromycin production method described herein, and (c) sealing the opening of the one or more containers, to produce the pharmaceutical dosage form.

The one or more containers preferably include one or more sterile vials, preferably glass vials, as described herein. The sealing step preferably includes sealing the opening using the means for aseptically sealing the opening described herein. The sealing means preferably includes a stopper as described herein. The liquid composition preferably contains azithromycin in an amount from about 10 mg/mL to about 500 mg/mL (e.g., from about 10 mg/mL to about 300 mg/mL, from about 25 mg/mL to about 250 mg/mL, from about 50 mg/mL to about 100 mg/mL, or from about 60 mg/mL to about 90 mg/mL). In a particularly preferred embodiment, the concentration of azithromycin in the liquid composition is about 74 mg/mL or about 75 mg/mL and the one or more containers (which are most preferably vials) are filled with about 10 mL or less (e.g., about 10 mL, about 8 mL, about 6 mL, about 4 mL, or about 1 mL) of the liquid composition, to provide a final dosage of from about 300 mg to about 700 mg of azithromycin, and especially a final dosage of about 500 mg of azithromycin. The method of preparing the inventive pharmaceutical dosage form can consistently and reproducibly produce dosage forms with high dosage accuracy and low variability in the dosage.

The pharmaceutical dosage form prepared in accordance with the present invention preferably is within about 20% of the label claim. In other words, the amount of azithromycin in the container (as determined by a suitable analytical technique, e.g., HPLC, azithromycin assay, or the like) preferably is within about 20 wt % of the azithromycin dosage claimed in the product label. Thus, for example, for 500 mg dosage vials prepared in accordance with the present invention, with a label claim of 500 mg of azithromycin, the amount of azithromycin in the vials, as determined by a suitable analytical technique, preferably is within about 400 mg to about 600 mg. Most preferably, the inventive pharmaceutical dosage form has an actual dosage of azithromycin that is within about 10% for its lower end and about 20% for its higher end of the label claim. Thus, for example, for 500 mg dosage vials prepared in accordance with the present invention, with a label claims of 500 mg of azithromycin, the amount of azithromycin in the vials is preferably within about 450 mg to about 600 mg. In another preferred embodiment, the inventive pharmaceutical dosage form has an actual dosage of azithromycin that is within about 15% of the label claim. Most preferably, the inventive pharmaceutical dosage form has an actual dosage of azithromycin that is within about 10% for its lower end and about 15% for its higher end of the label claim. Thus, for example, for 500 mg dosage vials prepared in accordance with the present invention, with a label claims of 500 mg of azithromycin, the amount of azithromycin in the vials is preferably within about 450 mg to about 575 mg.

Also provided by the invention is a method of treating a disease in a patient in need thereof. The method comprises dissolving the inventive pharmaceutical formulation comprising lyophilized azithromycin and ethanol in a pharmaceutically acceptable solvent to produce a pharmaceutically acceptable solution, and administering the solution to the patient. The lyophilized azithromycin formulation can be administered to a patient in need thereof (e.g., to treat microbial infections) using standard therapeutic methods for delivering azithromycin. While any suitable means of administering the pharmaceutical formulation to a human can be used within the context of the invention, typically and preferably the inventive method of treating a disease in a patient involves administering the pharmaceutical formulation to a human via injection. By the term "injection," it is meant that the composition is forcefully introduced into a target tissue of the human. The pharmaceutical formulation can be administered to the human by any suitable route, but preferably is administered to the human intravenously. When the inventive composition is administered by injecting, any suitable injection device can be used. While less preferred, other routes of administration can be used to deliver the pharmaceutical formulation to the human in accordance with the inventive method. Indeed, although more than one route can be used to administer the inventive formulation, a particular route can provide a more immediate and more effective reaction than another route.

The inventive pharmaceutical formulation comprising lyophilized azithromycin can be reconstituted for parenteral administration to a patient using any pharmaceutically acceptable diluent. Preferably, the diluent is Sterile Water for Injection, USP. Alternatively, the diluent may be, for example, sodium chloride solutions (e.g., 0.9% Sodium Chloride Injection, USP), dextrose solutions (e.g., 5% Dextrose for Injection), sodium chloride/dextrose mixtures (e.g., 5% Dextrose and 0.225% Sodium Chloride for Injection, 5% Dextrose and 0.45% Sodium Chloride for Injection), Lactated Ringer's for Injection, and mixtures thereof. Any quantity of diluent may be used to reconstitute the lyophilized azithromycin such that a suitable solution for injection is prepared. Accordingly, the quantity of diluent must be sufficient to dissolve the lyophilized azithromycin. Typically, about 10 mL or less (e.g., about 10 mL, about 8 mL, about 6 mL, about 4 mL, or about 1 mL) of diluent are used to reconstitute the lyophilized azithromycin formulation to yield a final concentration of about 100 mg/mL or less (e.g., about 90 mg/mL, about 70 mg/mL, about 50 mg/mL, about 30 mg/mL, or about 10 mg/mL). Most preferably, about 5 mL of diluent are used to reconstitute the lyophilized azithromycin formulation, such that the concentration of azithromycin in the solution is about 100 mg/mL. Prior to reconstitution, the inventive lyophilized azithromycin dosage form should be stored at controlled room temperature, preferably about 59° F. to about 86° F. (15° C. to 30° C.). Reconstituted solution is stable for 24 hours when stored below 30° C. or 86° F. Thus, if kept at room temperature, reconstituted solutions of the pharmaceutical formulation preferably are used within 24 hours.

Solutions of azithromycin may be further diluted after reconstitution using any suitable diluent. Suitable fluids for further dilution of solutions of reconstituted lyophilized azithromycin include, for example, Sterile Water for Injection, USP, sodium chloride solutions (e.g., 0.9% Sodium Chloride Injection, USP), dextrose solutions (e.g., 10% Dextrose for Injection), sodium chloride/dextrose mixtures (e.g., 5% Dextrose and 0.225% Sodium Chloride for Injection, 5% Dextrose and 0.45% Sodium Chloride for Injection), Lactated Ringer's for Injection, and mixtures thereof. Optimally, diluted reconstituted solutions of lyophilized azithromycin are administered to a patient promptly upon constitution. Alternatively, diluted reconstituted solutions preferably are refrigerated and used within seven days.

The inventive pharmaceutical formulation can be administered to a patient (i.e., a human patient) to treat or prevent any disease or condition against which azithromycin is active. In this regard, the pharmaceutical formulation can be administered to a human patient suffering from, for example, community-acquired pneumonia or pelvic inflammatory disease. In addition or alternatively, the inventive pharmaceutical formulation can be administered to a human patient that has been infected by a bacterium that is sensitive to azithromycin. Such microorganisms include, for example, *Staphylococcus aureus, Streptococcus pneumoniae, Streptococcus agalactiae, Streptococcus pyogenes, Haemophilus ducreyi, Haemophilus influenzae, Moraxella catarrhalis, Neisseria gonorrhoeae, Chlamydia pneumoniae, Chlamydia trachomatis, Legionella pneumrophila, Mycoplasma hominis,* and *Mycoplasma pneumoniae.* These microorganisms, however, are merely exemplary. Indeed, the inventive pharmaceutical formulation can be administered to a human patient that has been infected with any microorganism that is sensitive to (e.g., whose 50S ribosomal subunit is bound by and/or whose protein synthesis is interfered with by) azithromycin.

In addition to the preferred embodiments described herein, the inventive pharmaceutical formulation can comprise additional therapeutic or biologically active agents. For example, therapeutic factors useful in the treatment of a particular indication (e.g., pelvic inflammatory disease) can be present. Factors that control inflammation, such as ibuprofen or steroids, can be part of the composition to reduce swelling and inflammation associated with in vivo administration of the composition and physiological distress. Immune enhancers can be included in the composition to up regulate the body's natural defenses against disease. Vitamins and minerals, antioxidants, and micronutrients can be co-administered with the composition.

The following examples further illustrate the invention but, of course, should not be construed as in any way limiting its scope.

EXAMPLE 1

This example demonstrates the preparation of a liquid composition comprising an ethanolate of azithromycin, citric acid, and sodium hydroxide.

A quantity of sterile water for injection ("WFI") in an amount of 67.5 liters was collected (approximately 75% of total batch quantity) and was placed into a clean, jacketed glass-coated compounding tank. The temperature of the WFI was about 15° C. to 30° C. While stirring at 1052 rpm, 5.58 kg of citric acid, USP monohydrate was added to the WFI and mixed until the citric acid monohydrate was completely dissolved (at least 10 minutes). After dissolution of the citric acid monohydrate, 2.38 kg of sodium hydroxide, NF was added to the mixture and stirred at 1052 rpm until the sodium hydroxide was completely dissolved (at least 10 minutes). The resulting mixture (i.e., the compounding solution) was cooled to 24° C. Azithromycin raw material (obtained from a Teva-Tech, Ltd., 7.03 kg) was added to the compounding solution in the compounding tank. The resulting mixture was stirred at 1670 rpm until the azithromycin was completely dissolved in the compounding solution (at least 20 minutes). After the azithromycin was dissolved, the pH of the mixture was tested and adjusted to pH 6.5 with 850 mL of a 10% sodium hydroxide solution.

The batch volume was raised to 90 L (total batch quantity) by the addition of WFI, USP, and the solution was stirred at 740 rpm for at least an additional 10 minutes.

Prior to filtration, an in-process sample was taken from the batch tank, and was subjected to an appearance test (visual examination) and an azithromycin assay. After completion of the in-process appearance test and azithromycin assay, the cooled solution of azithromycin in compounding solution was mixed at 270 rpm and, while mixing, the solution was pumped through a 0.45 μm pre-filter ((Opticap™ Capsule available from Millipore Corporation) into a filling room using Tygon® tubing. The pre-filter was rinsed with WFI, USP prior to filtration of the azithromycin.

Following pre-filtration, the azithromycin solution was twice passed through a sterilizing 0.22 μm final filter (Opticap™ Capsule Hydrophilic PVDF membrane available from Millipore Corporation) and the filtrate was delivered into a clean, sterile receiving carboy using silicone tubing. Type I Flint glass vials (10 mL) were sterilized at 250° C. for at least 3 hours. In a class 100 clean room environment, the sterile vials were aseptically filled with approximately 7.3 mL of the solution and partially stoppered.

EXAMPLE 2

This example demonstrates a method of lyophilizing a pharmaceutical formulation comprising an ethanolate of azithromycin.

A nitrogen supply was connected to a sterilizing filter assembly on a lyophilizer, and the lyophilizer chamber and condenser were steam sterilized for at least 30 minutes using standard sterilization procedures. The minimum chamber drain temperature and minimum condenser drain temperature were each at least 121.0° C. After sterilization, a vessel integrity test was performed. The shelves and condenser plates of the lyophilizer were chilled to −30° C. and −50° C., respectively, the vacuum was pulled to below 100 micron Hg (13 Pa), and the vessel was leak tested.

The lyophilization process was initiated by pre-chilling the shelves of the lyophilizer. The shelf temperature controller was adjusted to a set point of 5° C. After the pre-chill set point was reached, the shelves were loaded with vials containing an azithromycin formulation prepared as described in Example 1 over an 8 hour period. After the product solution was completely loaded, the chamber door was closed and the shelf temperature was maintained at the pre-chill set point for at least 60 minutes. The shelf temperature controller was then adjusted to a set point of −40° C. with a ramp time of 225 minutes and the shelf temperature was held at the set point temperature of −40° C. for at least 4 hours.

The condenser was chilled below −50° C. When the condenser temperature reached −50° C., the primary drying step was performed. The vacuum controller set point was set to 80 micron Hg (11 Pa). Nitrogen gas was used to regulate the pressure. The shelf temperature controller was adjusted to a primary drying set point of 8° C. with a ramp time of 10 hours and the shelf temperature was held at the drying set point temperature of 8° C. for at least 36 hours.

The shelf temperature controller was adjusted to a first secondary drying set point of 35° C. with a ramp time of 540 minutes (9 hours), and the shelf temperature was held at the first secondary drying set point temperature of 35° C. for at least 15 hours. At the end of the 15-hour secondary drying hold time, the shelf temperature controller was adjusted to a second secondary drying set point of 45° C. with a ramp time of 100 minutes. The shelf temperature was held at the second secondary drying set point temperature of 45° C. for at least 18 hours. At the end of the secondary drying stage, the chamber was isolated and the vacuum was released to about 4 psi by addition of sterile nitrogen gas.

The vials containing the lyophilized azithromycin were then stoppered with Stelmi 6720 GC Gray Lyo stoppers using an internal stoppering mechanism. At the completion of the stoppering step, the chamber was again isolated and the vacuum released. The pressure was raised to atmospheric pressure by addition of sterile nitrogen gas. The lyophilizer chamber was unloaded and the stoppered vials containing lyophilized product were conveyed to a capping machine and sealed with aluminum seals. The vials were then inspected, labeled, and packaged.

The final product was a sterile, white to off-white solid having greater than 98% purity and was suitable for administration by injection. Solutions prepared by dissolving the final product in Sterile Water for Injection were clear and free of particulates.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of producing a stable, sterile pharmaceutical formulation comprising lyophilized azithromycin, which method comprises:
   (a) preparing a liquid composition comprising an ethanolate of azithromycin, an acid selected from the group consisting of citric acid, hydrochloric acid, lactic acid, glycolic acid, acetic acid, phosphoric acid, and tartaric acid, and an aqueous solvent,
   (b) chilling the composition to a temperature from about −10° C. to about 15° C., wherein the temperature is maintained for at least about 20 minutes to about 2 hours,
   (c) freezing the composition to a temperature of from about −30° C. to about −50° C., to produce a frozen mixture, wherein the temperature is maintained for at least about 1 hour,
   (d) subjecting the frozen mixture to a primary drying stage, which comprises applying a vacuum to reduce the pressure by an amount effective to remove aqueous solvent from the frozen mixture, and, while applying the vacuum, changing the temperature of the frozen mixture to a primary drying temperature, wherein the primary drying temperature is from about 0° C. to about 20° C., and wherein the primary drying temperature is maintained for at least about 20 hours to about 40 hours, to produce a first intermediate, and
   (e) subjecting the first intermediate to a secondary drying stage, which comprises applying a vacuum to reduce the pressure by an amount effective to remove aqueous solvent from the first intermediate, and, while applying the vacuum, (i) changing the temperature of the first intermediate to a first secondary drying temperature, wherein the first secondary drying temperature is from about 20° C. to about 40° C., and wherein the first secondary drying temperature is maintained for at least about 10 hours to about 20 hours, and (ii) changing the temperature of the first intermediate to a second secondary drying temperature, wherein the second secondary drying temperature is from about 30° C. to about 50° C., and wherein the second secondary drying temperature is maintained for at least about 10 hours to about 20 hours, to produce the pharmaceutical formulation, wherein ethanol is present in an amount from about 0.005% to about 0.5% by weight of the pharmaceutical formulation.

2. The method of claim 1, wherein the composition is chilled to a temperature from about 0° C. to about 10° C.

3. The method of claim 1, wherein the composition is frozen to a temperature of about −40° C.

4. The method of claim 1, wherein the primary drying temperature is about 8° C.

5. The method of claim 1, wherein the primary drying temperature in the primary drying stage is maintained for at least about 36 hours.

6. The method of claim 1, wherein the primary drying stage is carried out at a pressure of about 200 micron Hg or less.

7. The method of claim 6, wherein the primary drying stage is carried out at a pressure of about 80 micron Hg.

8. The method of claim 1, wherein the first secondary drying temperature is about 35° C.

9. The method of claim 1, wherein the second secondary drying temperature is about 45° C.

10. The method of claim 1, wherein the temperature of the frozen mixture in the secondary drying stage is changed at a rate of about 1° C. per minute or less.

11. The method of claim 10, wherein the temperature of the frozen mixture in the secondary drying stage is changed at a rate from about 0.05 to about 0.1° C. per minute.

12. The method of claim 1, wherein the first secondary drying temperature in the secondary drying stage is maintained for at least about 15 hours.

13. The method of claim 1, wherein the second secondary drying temperature in the secondary drying stage is maintained for at least about 18 hours.

14. The method of claim 1, wherein the secondary drying stage is carried out at a pressure of about 200 micron Hg or less.

15. The method of claim 14, wherein the secondary drying stage is carried out at a pressure of about 80 micron Hg.

16. The method of claim 1, wherein the composition is aseptically filtered and aseptically filled into a container after the completion of step (a) and before the completion of step (b).

17. A method of producing a stable, sterile pharmaceutical formulation comprising lyophilized azithromycin, which method comprises:
   (a) preparing a liquid composition comprising an ethanolate of Azithromycin, citric acid, and an aqueous solvent,
   (b) chilling the composition to a temperature from about −10° C. to about 15° C., wherein the temperature is maintained for at least about 20 minutes to about 2 hours,
   (c) freezing the composition to a temperature of from about 10° C. to about 70° C., to produce a frozen mixture, wherein the temperature is maintained for at least about 30 minutes to about 20 hours, (d) subjecting the frozen mixture to a primary drying stage, which comprises applying a vacuum to reduce the pressure by an amount effective to remove aqueous solvent from the frozen mixture, and, while applying the vacuum, changing the temperature of the frozen mixture to a primary drying temperature, wherein the primary drying temperature is from about −30° C. to about 20° C., and wherein the primary drying temperature is maintained for at least about 15 hours to about 50 hours, to produce a first intermediate, and (e) subjecting the first intermediate to a secondary drying stage, which comprises applying a vacuum to reduce the pressure by an amount effective to remove aqueous solvent from the first intermediate, and, while applying the vacuum, (i) changing the temperature of the first intermediate to a first secondary drying temperature, wherein the first secondary drying temperature is from about 0° C. to about 45° C., and wherein the first secondary drying temperature is maintained for at least about 5 hours to about 30 hours, and (ii) changing the temperature of the first intermediate to a second secondary drying temperature, wherein the second secondary drying temperature is from about 0° C. to about 60° C., and wherein the second secondary drying temperature is maintained for at least about 5 hours to about 30 hours, to produce the pharmaceutical formulation, wherein ethanol is present in an amount from about 0.005% to about 0.5% by weight of the pharmaceutical formulation.

* * * * *